United States Patent
Stepp et al.

(10) Patent No.: US 8,507,709 B2
(45) Date of Patent: Aug. 13, 2013

(54) METHOD FOR PRODUCING HYDROCARBON OXYSILICON COMPOUNDS

(75) Inventors: Michael Stepp, Ueberackern (AT); Markus Merget, Mehring (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/255,432

(22) PCT Filed: Mar. 19, 2010

(86) PCT No.: PCT/EP2010/053582
§ 371 (c)(1), (2), (4) Date: Sep. 8, 2011

(87) PCT Pub. No.: WO2010/112350
PCT Pub. Date: Oct. 7, 2010

(65) Prior Publication Data
US 2012/0010422 A1 Jan. 12, 2012

(30) Foreign Application Priority Data
Apr. 1, 2009 (DE) .......................... 10 2009 002 075

(51) Int. Cl.
*C07F 7/18* (2006.01)
(52) U.S. Cl.
USPC .......................................... 556/471; 556/470
(58) Field of Classification Search
USPC ........................ 556/423, 470, 471; 524/588
See application file for complete search history.

(56) References Cited

U.S. PATENT DOCUMENTS

| 2,967,171 A | | 1/1961 | Barnes, Jr. et al. |
| 3,417,120 A | | 12/1968 | Boissieras et al. |
| 5,310,842 A | * | 5/1994 | Ichinohe et al. ............ 528/12 |
| 6,005,131 A | * | 12/1999 | Jentsch et al. ............. 556/434 |
| 2003/0068890 A1 | | 4/2003 | Park |
| 2006/0041097 A1 | * | 2/2006 | Herrwerth et al. ............ 528/14 |

FOREIGN PATENT DOCUMENTS

| EP | 0475440 A2 | 3/1992 |
| JP | 8325277 A | 12/1996 |
| JP | 9012720 A | 1/1997 |

OTHER PUBLICATIONS

Mimoun, "Selective Reduction of Carbonyl Compounds by Polymethylhydrosiloxane in the Presence of Metal Hydride Catalysts", J. Org. Chem., vol. 64, pp. 2582-2589 (1999).
Sommer et al., "Stereochemistry of Asymmetric Silicon. XVI. Transition Metal Catalyzed Substitution Reactions of Optically Active Organosilicon Hydrides", Journal of the Amercan Chemical Society, vol. 91, No. 25, pp. 7061-7067 (1969).
Zhang et al., "Modification of polymethylhydrosiloxane by dehydrocoupling reactions catalyzed by transition metal complexes: Evidence for the preservation of linear siloxane structures", Silicon Chemistry, vol. 2, pp. 271-277 (2003).
PatBase Abstract of JP8325277A, Dec. 10, 1996.
PatBase Abstract of JP9012720A, Jan. 14, 1997.
International Search Report for PCT/EP2010/053582 dated May 21, 2010.
Van Der Post et al., "Diffuse Pollution of Water Sources by a Newly Identified Silicone Breakdown Product", Diffuse Pollution Conference, Dublin, pp. 8-40-8-43 (2003).

\* cited by examiner

*Primary Examiner* — Johann R Richter
*Assistant Examiner* — Pancham Bakshi
(74) *Attorney, Agent, or Firm* — Caesar, Rivise, Bernstein, Cohen & Pokotilow, Ltd.

(57) ABSTRACT

The invention relates to a method for producing silicon compounds (A) having hydrocarbon oxy-groups that have at least one unit of the general formula (1) $H_mSi(OR)_n(OR')_oR''pX4-m-n-o-p$ (1) by conversion of silicon compounds (B) having at least one unit of the general formula (2) $H_{m+n}Si(OR')oR''pX4-m-n-o-p$ (2), having an alcohol of the general formula (3) ROH (3) in the presence of a catalyst (K) that is on a carrier material bonded metal selected from Ni, Pd, Pt, wherein per mol formed group OR, at maximum 1 liter of solvent is used and wherein R, R', R", X, m, n, o and p have the meanings listed in claim 1.

19 Claims, No Drawings

METHOD FOR PRODUCING HYDROCARBON OXYSILICON COMPOUNDS

The invention relates to a process for preparing hydrocarbon-oxysilicon compounds by reacting SiH-silicon compounds with alcohols in the presence of metal catalysts on support materials.

Various processes for preparing alkoxysiloxanes are known from the prior art.

For example, JP 09040681 A carries out the hydrolysis of alkoxysilanes in the presence of a cation-exchange resin to form mixtures of alkoxysiloxanes having 2-5 Si atoms.

The formation of α,ω-dialkoxyoligosiloxanes by equilibration of linear or cyclic siloxanes with dialkoxysilanes in the presence of acids is described, for example, in JP 09012720 A.

A complicated route to 1,3-dimethoxy-1,1,3,3-tetramethyldisiloxane starting out from the corresponding α,ω-dichlorodisiloxane via ammonolysis, hydrolysis, esterification with methanol is described in JP 08325277 A.

The abovementioned processes have the disadvantage that they give mixtures of siloxanes from which the defined compounds, in particular the respective disiloxanes, have to be isolated in a complicated manner with large losses.

Silanes and siloxanes in which all or part of their valences are occupied by alkoxy groups can be prepared by reacting the corresponding SiH compounds with alcohols in the presence of basic, acidic or metal-containing catalysts with liberation of hydrogen. Here, the Si-bonded hydrogen atoms are replaced by the alkoxy radicals of the respective alcohol with liberation of gaseous hydrogen. Among the catalysts, there are representatives which not only accelerate the desired SiH exchange reaction but also cause undesirable secondary reactions such as equilibration or rearrangement of the siloxane skeleton. These strongly basic (e.g. metal alcoholates) or acidic catalysts are not suitable for targeted reactions, in particular in the presence of base- or acid-incompatible functional groups, so that alternatives which make a selective reaction possible have been sought.

A selection of such processes is, for example, disclosed in the following documents:

U.S. Pat. No. 2,967,171 describes the replacement of Si-bonded H by alkoxy groups by means of dehydrocondensation of SiH-silanes and SiH-siloxanes with alcohols. Hexachloroplatinic acid is used as catalyst, which is why only saturated systems can be used and entrainment of chloride ions or chlorine-containing compounds in the target product cannot be ruled out.

In EP 475440 A, a combination of a platinum compound and an organic acid serves as catalyst for the dehydrocondensation of SiH-siloxanes with an aliphatic alcohol having at least 4 carbon atoms. Entrainment of the organic acid in the target product cannot be ruled out.

DE 1248048 A describes the use of hydroxylamines as catalysts. However, here too, there is a risk of entrainment of organic constituents in the target product.

A catalytic system for the dehydrocondensation of SiH units with alcohols is described in EP 1627892. This is a mixture of a boron compound (e.g. tris(pentafluorophenyl) borane) and at least one synergistically acting metal salt. Entrainment of traces of metallic or boron-containing compounds in the target products can thus not be ruled out, as a result of which this route is not suitable for preparing, in particular, alkoxysiloxanes of semiconductor purity.

The dehydrocoupling of polyglycol alcohols with poly(methylhydrogen)siloxane can, according to Zhang, Ruzhi; Zhang, Zhengcheng; Amine, Khalil; West, Robert (Organosilicon Research Center, Department of Chemistry, University of Wisconsin-Madison, Madison, Wis., 53706, USA), Silicon Chemistry (2005), 2(5/6), 271-277) with Rh(PPh$_3$)$_3$Cl and Pd$_2$(dba)$_3$, be catalyzed without formation of branches.

Zinc hydrides have been described by H. Mimoun in Journal of Organic Chemistry (1999), 64(7), 2582-2589, as catalysts for, inter alia, the hydrosilylation of aldehydes, ketones and esters, but can also be used for the dehydrogenative silylation of alcohols. Their preparation from NaBH$_4$ and zinc carboxylates and their handling are complicated and demanding in terms of safety precautions.

All the abovementioned processes have the disadvantage that entrainment of traces of (co)catalysts in the target product can occur during isolation of the target products, and the products obtainable from these processes therefore have only limited suitability for use in applications in which impurities interfere, e.g. as CVD precursors in the semiconductor field. Some of the catalysts are not commercially available and have to be synthesized in a complicated and expensive manner. Recycling or reuse in the process is usually not possible.

L. H. Sommer and J. E. Lyons describe (Journal of the American Chemical Society 91, 7061 (1969)) the dehydrocondensation of optically active silanes with alcohols over heterogeneous catalysts, sometimes immobilized on support materials (e.g. palladium, ruthenium and rhodium on activated carbon). However, the reactions were carried out exclusively in the presence of nonpolar solvents, since these authors had indications that polar solvents poison the surface of the catalysts concerned.

It was an object of the invention to discover a process in which these disadvantages do not occur and which can be implemented using simple, preferably commercially available catalysts.

SUMMARY OF THE INVENTION

The invention provides a process for preparing silicon compounds (A) which have hydrocarbonoxy groups and have at least one unit of the general formula (1)

   (1)

by reacting silicon compounds (B) which have at least one unit of the general formula (2)

   (2)

with an alcohol of the general formula (3)

ROH   (3)

in the presence of a catalyst (K) which is metal selected from among Ni, Pd, Pt bound to a support material, where not more than one liter of solvent is used per mole of OR group formed and R is a monovalent hydrocarbon radical which has from 1 to 18 carbon atoms and may be substituted by OH groups, halogen atoms, silyl groups, siloxy groups, —CN, —COOR$^1$, —OCOOR$^2$, —CONR$^3$R$^4$, —OCONR$^5$R$^6$, —NR$^7$CONR$^8$R$^9$, —SO$_2$—R$^{10}$, —OSO$_2$—R$^{11}$, —OP(OR$^{12}$)(OR$^{13}$), where the carbon chain may be interrupted by nonadjacent —(CO)—, —O—, —S— or —NR$^{14}$— groups;

R', R" are each a monovalent hydrocarbon radical which has from 1 to 18 carbon atoms and may be substituted by halogen atoms, silyl groups, siloxy groups, —CN, —COOR$^1$, —OCOOR$^2$, —CONR$^3$R$^4$, —OCONR$^5$R$^6$, —NR$^7$CONR$^8$R$^9$, —SO$_2$—R$^{10}$, —OSO$_2$—R$^{11}$, —OP $(OR^{12})(OR^{13})$, where the carbon chain may be interrupted by nonadjacent —(CO)—, —O—, —S— or —$NR^{14}$— groups;

$R^1$ to $R^{14}$ are each a monovalent hydrocarbon radical which has from 1 to 18 carbon atoms and may be substituted by halogen atoms, X is a chemical bond via which radicals containing silicon atoms are bound, m is 0, 1, 2 or 3, n is 1, 2 or 3, m+n is 1, 2 or 3, o is 0, 1, 2 or 3, p is 0, 1, 2 or 3 and m+n+o+p is 1, 2, 3 or 4.

DETAILED DESCRIPTION OF PREFERRED EMBODIMENTS

It has surprisingly been found that the reaction of an SiH compound with alcohols in the presence of Ni, Pd, Pt on support materials in the presence of significantly smaller proportions up to complete absence of nonpolar solvents proceeds rapidly and spontaneously even under mild conditions and leads quantitatively with elimination of hydrogen to the corresponding alkoxysil(ox)ane and the ergonomics are thereby improved by an increase in the space-time yield. The further advantages of the process of the invention are that the insoluble heterogeneous catalyst can be separated off easily and completely by filtration, sedimentation, centrifugation or optionally by distilling off the target product and can be reused if required. The process of the invention is as a result predestined for the inexpensive preparation of particularly pure alkoxysil(ox)anes which are used, for example, in the semiconductor industry as CVD precursors. A further advantage is the substantial avoidance of secondary reactions which reduce the yield and produce wastes whose disposal pollutes the environment.

When m+n+o+p=4, i.e. 4-m-n-o-p=0, the silicon compounds (A) and (B) are monosilanes.

When m+n+o+p=1, 2 or 3, radicals containing silicon atoms are bound via the chemical bonds X in the units of the general formulae (1) and (2) in the silicon compounds (A) and (B).

The hydrocarbon radical R can be linear, cyclic, branched, aromatic, saturated or unsaturated. The hydrocarbon radical R preferably has from 1 to 6 carbon atoms, with particular preference being given to alkyl radicals, alkylaryl radicals, arylalkyl radicals and phenyl radicals. Particularly preferred alkyl radicals are methyl and ethyl. The hydrocarbon radical R preferably has no or from 1 to 6 additional OH groups, in particular 1, 2 or 3 OH groups. Only one OH group is present on a carbon atom.

The monovalent hydrocarbon radicals R', R" and $R^1$ to $R^{14}$ can be linear, cyclic, branched, aromatic, saturated or unsaturated. The hydrocarbon radicals R', R" and $R^1$ to $R^{14}$ preferably have from 1 to 6 carbon atoms, with particular preference being given to alkyl, vinyl, allyl and phenyl radicals. Particularly preferred alkyl radicals are methyl and ethyl.

The radicals bound via the chemical bonds X are preferably polyvalent hydrocarbon radicals $R^C$ which in the case of silicon compounds (A) have one or more units of the general formula (1) or in the case of silicon compounds (B) have one or more units of the general formula (2), preferably no or one unit of the general formula (1) or (2). The hydrocarbon radicals $R^C$ are preferably divalent, trivalent or tetravalent. The hydrocarbon radicals $R^C$ preferably have from 1 to 50, in particular from 1 to 18, particularly preferably from 1 to 6, for example 1, 2, 3 or 4, carbon atoms. The chemical bonds X are in this case Si—C bonds.

The radicals bound via the chemical bonds X are preferably monovalent or polyvalent hydrocarbon radicals $R^{CSi}$ which contain the silicon atoms bound via Si—C bonds. The silicon compounds (A) and (B) can comprise radicals $R^{CSi}$ and one or more units of the general formula (1) or (2). The hydrocarbon radicals $R^{CSi}$ are preferably divalent, trivalent or tetravalent. The radicals $R^{CSi}$ preferably have from 1 to 50, in particular from 1 to 18, particularly preferably from 1 to 6, for example 1, 2, 3 or 4, carbon atoms. The radicals $R^{CSi}$ preferably have from 1 to 10, particularly preferably from 1 to 6, for example 1, 2, 3 or 4, silicon atoms. The chemical bonds X are in this case Si—C bonds.

The radicals bound via the chemical bonds X are preferably monovalent or polyvalent (poly)silane radicals $R^{Si}$ which contain silicon atoms bound via Si—Si bonds. The silicon compounds (A) and (B) can comprise radicals $R^{Si}$ and one or more units of the general formula (1) or (2). The hydrocarbon radicals $R^{Si}$ are preferably divalent, trivalent or tetravalent. The radicals $R^{Si}$ preferably have from 1 to 50, in particular from 1 to 18, particularly preferably from 1 to 6, for example 1, 2, 3 or 4, silicon atoms. The radicals $R^{Si}$ preferably have from 1 to 10, particularly preferably from 1 to 6, for example 1, 2, 3 or 4, silicon atoms. The chemical bonds X are in this case Si—Si bonds.

The radicals bound via the chemical bonds X are preferably monovalent or polyvalent (poly)siloxane radicals $R^{OSi}$ which contain silicon atoms bound via Si—O—Si bonds. The (poly)siloxane radicals $R^{OSi}$ can be bound by the units of the general formulae (4), (5), (6) and/or (7)

$$(X')_b(R''')_c Si \qquad (4),$$

$$(X')_d(R''')_e SiO_{1/2} \qquad (5),$$

$$(X')_f(R''')_g SiO_{2/2} \qquad (6),$$

$$X'SiO_{3/2} \qquad (7),$$

to the units of the general formulae (1) and (2), where

X' is an —O— group,

R''' is as defined for R", b is 1, 2, 3 or 4, c is 0, 1, 2 or 3, b+c is 4, d is 1, 2 or 3, e is 0, 1 or 2, d+e is 3, f is 1 or 2, g is 0 or 1 and d+e is 2.

In this case, the chemical bonds X together with X' form Si—O—Si bonds.

The (poly)siloxane radicals $R^{OSi}$ can preferably contain up to 1000 further units of the general formulae (8), (9), (10) and (11)

$$R'''_3 SiO_{1/2} \qquad (8),$$

$$R'''_2 SiO_{2/2} \qquad (9),$$

$$R'''SiO_{3/2} \qquad (10),$$

$$SiO_{4/2} \qquad (11),$$

where

R''' is as defined above.

The silicon compounds (A) and (B) can comprise radicals $R^{OSi}$ and one or more units of the general formula (1) or (2). The radicals $R^{OSi}$ preferably have from 1 to 1000, in particular from 1 to 200, particularly preferably from 1 to 10, for example 1, 2, 3 or 4, units of the general formulae (4) to (11).

The silicon compounds (A) and (B) can be linear, cyclic or branched.

If the hydrocarbon radical R has further OH groups, two or more silicon compounds (A) can be joined or crosslinked via radicals R.

Preference is given to preparing silicon compounds (A) of the general formulae (12) to (15)

  (12),

  (13),

  (14),

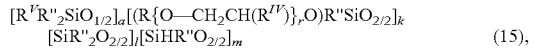  (15), where
$R^{IV}$ are hydrogen atoms or methyl radicals,
$R^V$ are methyl, ethyl, vinyl, allyl or phenyl radicals,
h is 1 or 2,
z is from 1 to 20,
y is 1, 2, 3 or 4,
a is from 0 to 2,
r is from 0 to 20,
k is from 1 to 20,
l is from 0 to 200,
m is from 0 to 100 and
a+k+l+m is at least 4 and
R and R" are as defined above.

In mixtures of the silicon compounds (A) of the general formulae (13) and (15), z, a, r, k, l, m can be averages and can therefore also be numbers with decimal places.

In the general formula (15), it is possible for units $[(R\{O—CH_2CH(R^{IV})\}_rO)R"SiO_{2/2}]_k$ in which the radicals $R^{IV}$ are exclusively hydrogen atoms or methyl radicals or in which the radicals $R^{iv}$ are mixed hydrogen atoms and methyl radicals to occur. All mixing ratios of hydrogen atoms/methyl radicals from 0 to 100% of hydrogen atoms are possible.

The variety of the silicon compounds (A) which can be obtained by the process of the invention is indicated by the following examples:
(tBuO)HSi(OEt)$_2$, MeO—Si(n-Bu)$_3$, (MeOSiMe$_2$)$_2$—CH—CH—(SiMe$_2$OMe)$_2$,
(MeO)$_3$Si—O—CH$_2$CH$_2$—O—Si(OMe)$_3$, (EtO)$_3$Si—O—CH$_2$CH(CH$_3$)—O—Si(OEt)$_3$,
PhO—SiPh(OMe)$_2$, n-cyclohexyl—O—SiMe(OEt)$_2$, HO—CH$_2$CH$_2$—O—SiMe$_2$(O—CH$_2$CH$_2$—O—CH$_2$CH$_2$—O—CH$_2$CH$_2$—OMe), HO—CH$_2$—SiMe$_2$-O—SiMe$_2$-CH$_2$—O—SiMe$_2$-O—SiMe$_2$-O—CH$_2$—SiMe$_2$-O—SiMe$_2$-CH$_2$—OH,
Me—CH$_2$CH$_2$O—CH$_2$CH$_2$O—CH$_2$CH$_2$O—CH$_2$CH$_2$O—SiMe$_2$O—SiMe$_2$O—SiMe$_2$O—SiMe$_2$O—SiMe$_2$-CH=CH$_2$,
tBuOSi(OEt)$_2$-CH$_2$—Si(OEt)$_2$H, (EtO)$_3$Si—O—CH$_2$CH(CH$_3$)—O—Si(OEt)$_3$MeO—SiMe$_2$-O—SiMe$_2$-OMe, (MeO—SiMeO)$_4$, (EtO—SiMeO)$_5$,
(Me$_2$SiO)$_3$(Si(tBuO)MeO), (MeO—SiMe$_2$-O)$_4$Si, (MeO—SiMe$_2$-O)$_3$SiMe, (PhO—SiMe$_2$-O)$_3$SiPh,
Me$_3$Si—O—SiMe$_2$-O—CH$_2$CH$_2$—O—H$_2$CH$_2$—O—CH$_2$CH$_2$—CH$_2$CH$_2$OMe,
MeO—SiMe$_2$O—(SiMe$_2$O)$_{35}$—SiMe$_2$-OMe,
Me$_3$SiO—(SiHMeO)$_{35}$—(Si(OEt)MeO)$_{20}$—SiMe$_3$,
Me$_3$SiO—(SiMe$_2$O)$_{220}$(Si(O-iPr)MeO)$_5$—SiMe$_3$ H$_2$C=CH—CH$_2$—O—CH$_2$CH$_2$—O—SiMe$_2$O—(SiMe$_2$O)140(SiHMeO)$_5$—SiMe$_2$-O—CH$_2$CH$_2$—O—CH$_2$—CH=CH$_2$
(EtO)$_3$Si—O—(SiMe$_2$O)$_{495}$—Si(OEt)$_3$
[Me$_3$SiO$_{1/2}$]$_4$[SiMeO$_{3/2}$]$_{7.5}$[SiMe(OEt)O$_{1/2}$]$_4$[SiMeHO$_{2/2}$]$_1$
[(EtO)$_3$SiO$_{1/2}$]$_6$[(EtO)$_2$SiO$_{2/2}$]$_{4.6}$[HSi(OEt)O$_{2/2}$]$_{1.4}$
[HSiO$_{3/2}$]
[SiO$_{4/2}$]$_1$
H$_2$C=CH—SiMe$_2$O—(SiMe$_2$O)$_{440}$(Si[O—(CH$_2$CH$_2$O)$_3$-Me]MeO)$_{14}$—SiMe$_2$-CH=CH$_2$
Me$_3$SiO—(SiMe(CH=CH$_2$)O)$_{4.9}$—(SiMe$_2$O)$_{12}$—(Si[O—(CH$_2$)$_9$—CH=CH$_2$]MeO)$_{8.3}$—SiMe$_3$
Me$_3$SiO—(SiMeCH$_2$CH$_2$CF$_3$O)$_{15.2}$(Si[O-n-dodecyl]MeO)$_7$—SiMe$_3$H$_2$C=CH—SiMe$_2$O—
(SiMe{OCH$_2$CH$_2$CH$_2$OCH$_2$CH$_2$OCH$_2$CH$_2$OCH$_2$CH$_2$OMe}O)$_6$(Si(OEt)MeO)$_2$—SiMe$_2$-CH=CH$_2$ A notable aspect of the process of the invention is that the part of the molecule of the silicon compounds (B) which is not affected by the dehydrocondensation reaction with the alcohol of the general formula (3) is generally not changed or changed only insignificantly by the reaction to form silicon compounds (A). Possible changes to the molecular skeleton are restricted essentially to minor secondary reactions such as condensation reactions of silanol groups which are formed by hydrolysis reactions. The water necessary for this can, for example, be introduced into the reaction via the reaction components. Accordingly, only the units of the general formula (2) present in silicon compounds (B) are, depending on stoichiometry and reaction conditions, converted completely or partly into units of the general formula (1). The silicon compounds (A) accordingly differ from the silicon compounds (B) essentially in the units of the general formula (1) formed from the units of the general formula (2) in the process of the invention.

Examples of silicon compounds (B) are:
HSi(n-Bu)$_3$, H$_2$Si(OEt)$_2$, (HSiMe$_2$)$_2$—CH—CH—(SiMe$_2$H)$_2$, HSi(OMe)$_3$,
HSi(OEt)$_3$, HSiPh(OMe)$_2$, HSiMe(OEt)$_2$, HSiMe$_2$(O—CH$_2$CH$_2$—O—CH$_2$CH$_2$—O—CH$_2$CH$_2$—OMe),
H—SiMe$_2$O—SiMe$_2$O—SiMe$_2$O—SiMe$_2$O—SiMe$_2$-CH=CH$_2$,
HSi(OEt)$_2$-OH$_2$—Si(OEt)$_2$H, HSi(OEt)$_2$-O—CH$_2$CH(CH$_3$)—O—Si(OEt)$_2$H
H—SiMe$_2$-O—SiMe$_2$-H, (H—SiMeO)$_4$, (H—SiMeO)$_5$, (Me$_2$SiO)$_3$(SiHMeO),
(H—SiMe$_2$-O)$_4$Si, (H—SiMe$_2$-O)$_3$SiMe, (H—SiMe$_2$-O)$_3$SiPh,
Me$_3$Si—O—SiMe$_2$-H,
H—SiMe$_2$O—(SiMe$_2$O)$_{35}$—SiMe$_2$-H, Me$_3$SiO—(SiHMeO)$_{55}$—SiMe$_3$,
Me$_3$SiO—(SiMe$_2$O)$_{220}$(SiHMeO)$_5$—SiMe$_3$
H—SiMe$_2$O—(SiMe$_2$O)$_{140}$(SiHMeO)$_5$—SiMe$_2$-H
HSi(OEt)$_2$-O—(SiMe$_2$O)$_{495}$—Si(OEt)$_2$-H
[Me$_3$SiO$_{1/2}$]$_4$[SiMeO$_{3/2}$]$_{7.5}$[SiMe(OEt)O$_{1/2}$]$_2$[SiMeHO$_{2/2}$]$_6$
[HSi(OEt)$_2$O$_{1/2}$]$_6$[HSi(OEt)O$_{2/2}$]$_5$[HSiO$_{3/2}$]$_{2.2}$[SiO$_{4/2}$]$_1$
H$_2$C=CH—SiMe$_2$O—(SiMe$_2$O)$_{440}$(SiHMeO)$_{14}$—SiMe$_2$-CH=CH$_2$
Me$_3$SiO—(SiMe(CH=CH$_2$)O)$_{4.9}$—(SiMe$_2$O)$_{12}$—(SiHMeO)$_{8.3}$—SiMe$_3$
Me$_3$SiO—(SiMeCH$_2$CH$_2$CF$_3$O)$_{15.2}$(SiHMeO)$_7$—SiMe$_3$
H$_2$C=CH—SiMe$_2$O—
(SiMe{OCH$_2$CH$_2$CH$_2$OCH$_2$CH$_2$OCH$_2$CH$_2$OCH$_2$CH$_2$OMe}O)$_6$
(SiHMeO)$_2$—SiMe$_2$-CH=CH$_2$ Numbers with decimal places in the examples of silicon compounds (A) and (B) are average values for mixtures of silicon compounds (A) or (B).

Examples of alcohols of the general formula (3) are: Methanol, ethanol, 2-propanol, 1-propanol, 1butanol, 2-butanol, 2-methyl-2-propanol, 2-methyl-1-propanol, 1-pentanol, 1-hexanol, 1,2-ethanediol, 1-methyl-1,2-ethanediol, 2,5-dimethyl-2,5-hexanediol, 2-butene-1,4-diol, 2-butyne-1,4-diol, 3-hexyne-2,5-diol, the neopentyl glycol ester of hydroxypivalinic acid, neopentyl glycol, poly-THF-1000® (BASF) (=H[OCH$_2$CH$_2$CH$_2$CH$_2$]$_n$OH), 1-ethynyl-1-cyclohexanol, 2-methyl-3-butyn-2-ol, 4-ethyl-1-octyn-3-ol, 2-chloro-ethanol, propargyl alcohol, t-amyl alcohol, N-(2-hydroxyethyl)-2-pyrrolidone, 1,4-butanediol, 2,4-butanediol, 2-ethylhexanol, furfuryl alcohol, glycerol, 1,3-propanediol, 10-undecen-1-yl, 1-dodecanol, 1-octadecanol, allyl alcohol, allyl-PEG-OH having an average of 3 PEG units, 2-hydroxy-1-ethyl methacrylate, ethyl lactate, HO—CH$_2$—SiMe$_2$-O—SiMe$_2$-CH$_2$—OH, HO—CH$_2$CH$_2$CH$_2$—SiMe$_2$-O—SiMe$_2$-CH$_2$CH$_2$CH$_2$—OH.

Catalysts (K) used in the process of the invention are the metals of Ni, Pd, Pt immobilized on support materials.

Suitable support materials are in principle all inorganic or organic polymers used hitherto for this purpose in the prior art, e.g. SiO$_2$, Al$_2$O$_3$, aluminas, activated carbons, zeolites or organic resins. The catalyst support material is preferably activated carbon or Al$_2$O$_3$, with palladium/activated carbon, palladium/Al$_2$O$_3$ and nickel/activated carbon, in particular palladium/activated carbon, being preferred as catalysts (K). The catalysts used are commercial products or can be produced by processes customary in metal-organic chemistry. The concentration of the metal bound to the support material is preferably in the range of at least 0.01% by weight, particularly preferably at least 0.1% by weight, in particular at least one and not more than 30% by weight, particularly preferably not more than 10% by weight and in particular not more than 6% by weight. Catalysts (K) having higher metal concentrations can effloresce and contaminate the silicon compound (A) with metallic constituents (this applies particularly when the silicon compound (A) cannot be distilled), and in the case of catalysts (K) having lower metal concentrations, higher proportions by weight of catalyst are necessary because of the reduced specific activity, as a result of which the work-up can be more complicated and/or losses can occur due to adsorption of silicon compounds (A) on the catalyst (K).

The catalysts (K) can contain certain proportions of water. The drier the catalysts, the more reactive they generally are, especially in air or in contact with organic materials. To suppress undesirable reactions resulting therefrom which can have consequences through to spontaneous ignition, especially in the handling of the pure catalysts (K), the solid catalysts are sometimes produced with a certain water content. The proportion of water can originate from the production of the catalyst (K) or can be deliberately added. The process of the invention is preferably carried out using catalysts (K) having a water content which does not lead to any undesirable secondary reactions but is sufficient to ensure safe handling of the catalyst (K). The water content of catalysts (K) having activated carbon as support material is preferably at least 0.1% by weight, particularly preferably at least 1% by weight, in particular at least 10% by weight, and not more than 90% by weight, particularly preferably not more than 70% by weight, in particular not more than 60% by weight.

The catalysts (K) can be introduced into the reaction either directly as solid or as a suspension in one of the two reactants silicon compound (B) or alcohol of the general formula (3) or the target product component (A) or a suitable solvent.

The catalyst (K) bound to a support material is preferably removed after the reaction is complete or at the end of the process of the invention by filtration, decantation or centrifugation and can optionally be reused or recycled.

The amount of catalyst used depends on the number of units of the general formula (2) present in the silicon compounds (B). The catalyst (K) is preferably used in amounts of at least 10 ppm, particularly preferably at least 20 ppm, in particular at least 50 ppm, and not more than 10 000 ppm, particularly preferably not more than 1000 ppm and in particular not more than 700 ppm, calculated as metallic element and based on the total weight of the silicon compounds (B). The optimal concentration with regard to reaction rate or economics can be determined in simple preliminary tests by, for example, placing a partial amount of silicon compound (B) together with the alcohol of the general formula (3) in a reaction vessel and adding catalyst (K) until clearly discernible hydrogen evolution commences.

The amount of alcohol of the general formula (3) used depends on the number of units of the general formula (2) in the silicon compounds (B) and the desired degree of conversion. If complete conversion is desired, the alcohol of the general formula (3) is used in an equimolar amount or in an excess relative to the units of the general formula (2) present in the silicon compounds (B).

The amount of alcohol of the general formula (3) used is preferably at least 1 mol and not more than 4 mol, particularly preferably not more than 3 mol and in particular not more than 2 mol, of OH per 1 mol of the Si-bonded H atoms having the index n in the units of the general formula (2) to be reacted in the silicon compounds (B). If incomplete conversion is desired, i.e. m>0, it is also possible to use, for example, smaller proportions of alcohol.

The process of the invention is preferably carried out at a temperature of at least −10° C., particularly preferably at least +10° C., in particular at least +20° C., and not more than +200° C., particularly preferably not more than +120° C., in particular not more than +100° C. If the boiling point of the lowest-boiling component is below the reaction temperature desired for an ideally fast reaction, the reaction can be carried out under superatmospheric pressure. In the case of exothermic reactions, it can be useful to remove the unusable heat of reaction by cooling (jacket cooling or evaporative cooling).

The process of the invention is preferably carried out under an absolute pressure of at least 10 hPa, particularly preferably at least 100 hPa, and not more than 4000 hPa, particularly preferably not more than 2000 hPa. In particular, the process of the invention is carried out at the pressure of the surrounding atmosphere. The hydrogen formed during the reaction can be used completely or partly for building up the pressure. For technical reasons, it may be advantageous to allow the hydrogen formed in the reaction to be given off during the reaction.

When the reactants silicon compound (B), the alcohol of the general formula (3) and the catalyst (K) are mixed, the desired reaction generally commences spontaneously with evolution of hydrogen in the abovementioned temperature range in the process of the invention. For safety reasons, it can therefore be advantageous not to mix the total amount but instead to place one of the two reactants together with the catalyst (K) in a reaction vessel and introduce the other reactant at such a rate that the gas evolution can be controlled. As an alternative, the catalyst (K) can be placed in a reaction vessel and a mixture of both reactants can be introduced or each reactant can be introduced separately but in parallel. If only part of the units of the general formula (2) present in silicon compound (B) or only part of the silicon compound (B) is to be reacted, preference is given to placing the silicon compound (B) together with the catalyst (K) in a reaction vessel and introducing the alcohol of the general formula (3). In the case of reaction mixtures which react only sluggishly because of kinetic effects, e.g. because of steric hindrance, incomplete miscibility, it is also possible to mix the total amount of all reactants including the catalyst (K) and allow the mixture to react until the desired degree of conversion has been achieved. The degree of conversion of the mixture can be monitored with the aid of the gas evolution, e.g. by volumetric determination of the amount of hydrogen liberated, or by means of the customary analytical methods such as hydrogen content titration, gas chromatography, infrared, Raman, NMR spectroscopy on the reaction mixture. Complete reaction of the total alcohol of the general formula (3) and/or all units of the general formula (2) in the reaction can easily be recognized by the end of gas evolution.

In principle, mixtures of various silicon compounds (B) and/or mixtures of alcohols of the general formula (3) can be used in the process of the invention.

Mixed silicon compounds (A) can also be obtained by the process of the invention by means of successive reaction of the component (B) with various alcohols of the general formula (3), with the proportion of the respective radical R in the silicon compounds (A) being able to be set via the stoichiometric ratio of alcohol of the general formula (3) to units of the general formula (2). For example, 30% of all units of the general formula (2) can firstly be reacted with an alcohol 1 and the remaining 70% of the units of the general formula (2) can subsequently be reacted with an alcohol 2.

In principle, it is possible in the process of the invention to stop the reaction of silicon compounds (2) with the alcohol of the general formula (3) by deactivating and/or separating off the catalyst (K), separating off the alcohol and/or the silicon compounds (B) and/or the silicon compounds (A) from the reaction mixture before complete conversion has been reached. The solid catalyst (K) can be separated off by the methods customary for the removal of solids, e.g. filtration, sedimentation, centrifugation. The silicon compounds (A) and (B) and alcohol of the general formula (3) can, if they are solids, be separated off together with the catalyst (K) by the methods described for the purpose or by distillation, extraction, adsorption or reaction with a scavenging reagent, for example a chlorosilane or hexamethyldisilazane for removal of the alcohol of the general formula (3).

After the desired conversion has been reached with removal of the catalyst (K) and/or the other silicon compounds (A), (B) still present, the reaction mixture is preferably worked up and the silicon compound (A) is particularly preferably purified by separating off undesirable secondary constituents, e.g. by heating to remove volatile components or distillation. However, the reaction mixture can also be passed directly without work-up to further processing or use.

Preference is given to using not more than 0.5 liter, particularly preferably not more than 0.1 liter, in particular not more than 0.01 liter, in particular not more than 0.001 liter, of solvent per mole of OR group formed.

Solvents, for example, aliphatic and aromatic hydrocarbons such as n-pentane, n-heptane, isooctane, alkane mixtures, benzene, toluene, o-xylene, p-xylene and m-xylene; chlorinated hydrocarbons such as dichloromethane, trichloromethane, chlorobenzene; ethers such as diethyl ether, diisopropyl ether, di-n-butyl ether, tetrahydrofuran, dioxane, ethylene glycol dimethyl ether, diethylene glycol dimethyl ether, triethylene glycol dimethyl ether, polyethylene glycol dimethyl ether, methyl t-butyl ether; silicone oils such as hexamethyldisiloxane, polymethyldisiloxanes having trimethylsilyl end groups and viscosities of 2-100 mPas at 20° C.; cyclic siloxanes such as octamethylcyclotetrasiloxane, decamethylcyclopentasiloxane; and solvent mixtures can be used in the process of the invention, for example for compatibilizing poorly miscible or immiscible reactants or for reducing the viscosity, but are preferably present only in the case of polymers having a viscosity of >100 mPas at 20° C. and/or alcohols having a molar mass of >75 g/mol. Particular preference is given to not using any solvents in the process of the invention.

In principle, the process can be carried out in a batch, semibatch or continuous mode. Particularly in the case of a continuous process, it can be useful to use the catalyst (K) as a fixed bed and pass the mixture of the reactants in gaseous, liquid or dissolved form over the catalyst.

All above symbols in the above formulae in each case have their meanings independently of one another. In all formulae, the silicon atom is tetravalent.

Unless indicated otherwise, all amounts and percentages are by weight, all pressures are 0.10 MPa (abs.) and all temperatures are 20° C. in the following examples.

EXAMPLE 1A

Preparation of
1,3-dimethoxy-1,1,3,3-tetramethyldisiloxane

In a 500 ml four-neck flask provided with reflux condenser, precision glass stirrer and thermometer, 2.12 g of 5% palladium on activated carbon, water-free (commercially available from Sigma-Aldrich Corp., USA) were suspended in 150 g of methanol. This mixture was heated to 50° C. on an oil bath. At this temperature, 212.5 g of 1,1,3,3-tetramethyldisiloxane were subsequently introduced over a period of 2.5 hours while stirring. After addition of the first drops of the SiH-functional siloxane, spontaneous hydrogen evolution commenced. After the addition was complete, the mixture was allowed to react further for 15 minutes, the black precipitate was filtered off on a pressure filter and the colorless clear filtrate was distilled via a 35 cm packed column. After the first fraction, which according to gas-chromatographic analysis consisted mainly of methanol, 248.9 g of 1,3-dimethoxy-1,1, 3,3-tetramethyldisiloxane (viz. 81% of theory) having a purity of 99% according to gas-chromatographic analysis distilled over at a boiling temperature of 139° C. The total chlorine content was determined by means of ashing and coulometry and was below the detection limit of 3 ppm. The product is thus suitable for use in semiconductor applications.

EXAMPLE 1B

Preparation of
1,3-dimethoxy-1,1,3,3-tetramethyldisiloxane

Example 1a was repeated with the modification that 2.12 g of 5% palladium on activated carbon containing 54.9% by weight of water (commercially available from Johnson & Matthey, UK, as Pd on charcoal type 87 L) was used as catalyst. The target product was isolated in a yield of 85% of theory by distillation. Its purity was 99.4% according to gas-chromatographic analysis. The total chlorine content was determined by means of ashing and coulometry and was below the detection limit of 3 ppm.

The product is thus likewise suitable for use in semiconductor applications.

EXAMPLE 2

Preparation of tetrakis(1,1-dimethyl-1-methoxy-siloxy)silane

In a 500 ml four-neck flask provided with reflux condenser, precision glass stirrer and thermometer, 0.75 g of 5% palladium on activated carbon, water-free (commercially available from Sigma-Aldrich Corp., USA) was suspended in 87.8 g of methanol. This mixture was heated to 50° C. on an oil bath. At this temperature, 150 g of tetrakis(1,1-dimethylsiloxy)silane was subsequently introduced over a period of 3 hours while stirring. After addition of the first drops of the SiH-functional siloxane, spontaneous hydrogen evolution commenced. After the addition was complete, the mixture was allowed to react further for 15 minutes, the black precipitate was filtered off on a pressure filter and the colorless clear filtrate was distilled via a 35 cm packed column. After the first fraction, which according to gas-chromatographic analysis consisted mainly of methanol, 26.7 g of pure tetrakis(1,1-dimethyl-1-methoxysiloxy)silane distilled over at a boiling temperature of 120° C. at 12 hPa.

EXAMPLE 3

Preparation of tri-n-butylmethoxysilane

In a 500 ml four-neck flask provided with reflux condenser, precision glass stirrer and thermometer, 1.2 g of 5% palladium on activated carbon, water-free (commercially available from Sigma-Aldrich Corp., USA) were suspended in 23.7 g of methanol. 124 g of tri-n-butylsilane (prepared from trichlorosilane and n-butylmagnesium chloride by a method customary in organic chemistry) were subsequently introduced at room temperature over a period of one hour while stirring. After addition of the first drops of the SiH-functional siloxane, spontaneous hydrogen evolution commenced. The temperature of the reaction mixture rose to a maximum of 35° C. After the addition was complete, the mixture was allowed to react further until gas evolution could no longer be observed at the attached bubble counter, the black precipitate was filtered on a pressure filter and the colorless clear filtrate was distilled via a 20 cm Vigreux column. After the first fraction, which according to gas-chromatographic analysis consisted mainly of methanol, 134 g of tributylmethoxysilane having a GC purity of 99.5% by area distilled over at a boiling temperature of 112° C. at 10 hPa.

EXAMPLE 4

Preparation of a reaction product of H-siloxane polymethyl(H)siloxane with 2-ethylhexan-1-ol In a 100 ml three-neck flask provided with reflux condenser, magnetic stirrer and thermometer, 20 g of a methyl-H-polysiloxane of the average formula: $[Me_3SiO_{1/2}]_2[MeSiHO]_{55}$ were admixed with 0.1 g of 5% palladium on activated carbon, water-free (commercially available from Fluka/Aldrich). The mixture was subsequently heated to 70° C. on an oil bath. 2.1 g of 2-ethylhexan-1-ol were introduced over a period of one minute while stirring. The mixture was stirred at 100° C. for 8 hours, then cooled and filtered. Heating of the clear colorless filtrate at 100° C./10 mbar gave a polysiloxane which on the basis of $^1$H— and $^{29}$Si—NMR was assigned the following average formula: $[Me_3SiO_{1/2}]_2[MeSiHO]_{54}[MeSi(O—CH_2CH(CH_2CH_3)—CH_2CH_2CH_2CH_3)O]_1$, the palladium content was below the detection limit of 0.5 ppm, the total chorine content was below the detection limit of 3 ppm.

The invention claimed is:

1. A process for preparing silicon compound products which have hydrocarbonoxy groups and have at least one unit of the general formula (1)

$$H_mSi(OR)_n(OR')_oR''_pX_{4-m-n-o-p} \quad (1)$$

said method comprising reacting silicon compound reactants which have at least one unit of the general formula (2)

$$H_{m+n}Si(OR')_oR''_pX_{4-m-n-o-p} \quad (2)$$

with an alcohol of the general formula (3)

$$ROH \quad (3)$$

in the presence of a catalyst which is a metal selected from the group consisting of Ni, Pd and Pt bound to a support material, where not more than one liter of solvent is used per mole of OR group formed and R is a monovalent hydrocarbon radical which has from 1 to 18 carbon atoms and is optionally substituted by OH groups, halogen atoms, silyl groups, siloxy groups, —CN, —COOR$^1$, —OCOOR$^2$, —CONR$^3$R$^4$, —OCONR$^5$R$^6$, —NR$^7$CONR$^8$R$^9$, —SO$_2$—R$^{10}$, —OSO$_2$—R$^{11}$, —OP(OR$^{12}$)(OR$^{13}$), where a carbon chain thereof is optionally interrupted by nonadjacent —(CO)—, —O—, —S— or —NR$^{14}$— groups;

R', R" are each a monovalent hydrocarbon radical which has from 1 to 18 carbon atoms and is optionally substituted by halogen atoms, silyl groups, siloxy groups, —CN, —COOR$^1$, —OCOOR$^2$, —CONR$^3$R$^4$, —OCONR$^5$R$^6$, —NR$^7$CONR$^8$R$^9$, —SO$_2$—R$^{10}$, OSO$_2$—R$^{11}$, —OP(OR$^{12}$)(OR$^{13}$), where a carbon chain thereof is optionally interrupted by nonadjacent —(CO)—, —O—, —S— or —NR$^{14}$— groups;

R$^1$ to R$^{14}$ are each a monovalent hydrocarbon radical which has from 1 to 18 carbon atoms and is optionally substituted by halogen atoms, X is a chemical bond via which radicals containing silicon atoms are bound, m is 0, 1, 2 or 3, n is 1, 2 or 3, m+n is 1, 2 or 3, o is 0, 1, 2 or 3, p is 0, 1, 2 or 3 and m+n+o+p is 1, 2, 3 or 4.

2. The process as claimed in claim 1, wherein the hydrocarbon radical R has from 1 to 6 carbon atoms and no additional OH group.

3. The process as claimed in claim 1, wherein the radicals bound via chemical bonds X are polyvalent hydrocarbon radicals R$^C$ which in the case of silicon compound products have one or more units of the general formula (1) and in the case of silicon compound reactants have one or more units of the general formula (2).

4. The process as claimed in claim 1, wherein the radicals bound via the chemical bonds X are monovalent or polyvalent hydrocarbon radicals R$^{CSi}$ which contain silicon atoms bound via Si—C bonds.

5. The process as claimed in claim 1, wherein the radicals bound via the chemical bonds X are monovalent or polyvalent (poly)silane radicals R$^{Si}$ which contain silicon atoms bound via Si—Si bonds.

6. The process as claimed in claim 1, wherein the radicals bound via the chemical bonds X are monovalent or polyvalent (poly)siloxane radicals R$^{OSi}$ which contain silicon atoms bound via Si—O—Si bonds.

7. The process as claimed in claim 1, wherein the silicon compound products selected from among the general formulae (12) to (15)

$$(RO)_h\text{—}SiR''_{4-h} \quad (12),$$

$$RO\text{—}[SiR''_2\text{—}O\text{—}]_z\text{—}R \quad (13),$$

$$[RO\text{—}SiR''_2\text{—}O]_y Si\text{—}R''_{4-y} \quad (14),$$

$$[R^V R''_2 SiO_{1/2}]_a [(R\{O\text{—}CH_2CH(R^{IV})\}_r O)R''SiO_{2/2}]_k [SiR''_2 O_{2/2}]_l [SiHR''O_{2/2}]_m \quad (15),$$

are prepared, where
$R^{IV}$ are hydrogen atoms or methyl radicals,
$R^V$ are methyl, ethyl, vinyl, allyl or phenyl radicals,
h is 1 or 2,
z is from 1 to 20,
y is 1, 2, 3 or 4,
a is from 0 to 2,
r is from 0 to 20,
k is from 1 to 20,
l is from 0 to 200,
m is from 0 to 100 and
a+k+l+m is at least 4.

8. The process as claimed in claim 1, wherein the catalyst support materials are selected from the group consisting of $SiO_2$, $Al_2O_3$, aluminas, activated carbons, zeolites and organic resins.

9. The process as claimed in claim 1, wherein a temperature is from −10° C. to +200° C.

10. The process as claimed in claim 1 which is carried out in a batch, semibatch or continuous mode of operation.

11. The process as claimed in claim 2, wherein the radicals bound via chemical bonds X are polyvalent hydrocarbon radicals $R^C$ which in the case of silicon compound products have one or more units of the general formula (1) and in the case of silicon compound reactants have one or more units of the general formula (2).

12. The process as claimed in claim 2, wherein the radicals bound via the chemical bonds X are monovalent or polyvalent hydrocarbon radicals $R^{CSi}$ which contain silicon atoms bound via Si—C bonds.

13. The process as claimed in claim 2, wherein the radicals bound via the chemical bonds X are monovalent or polyvalent (poly)silane radicals $R^{Si}$ which contain silicon atoms bound via Si—Si bonds.

14. The process as claimed in claim 2, wherein the radicals bound via the chemical bonds X are monovalent or polyvalent (poly)siloxane radicals $R^{OSi}$ which contain silicon atoms bound via Si—O—Si bonds.

15. The process as claimed in claim 2, wherein the silicon compound products selected from among the general formulae (12) to (15)

$$(RO)_h\text{—}SiR''_{4-h} \quad (12),$$

$$RO\text{—}[SiR''_2\text{—}O\text{—}]_z\text{—}R \quad (13),$$

$$[RO\text{—}SiR''_2\text{—}O]_y Si\text{—}R''_{4-y} \quad (14),$$

$$[R^V R''_2 SiO_{1/2}]_a [(R\{O\text{—}CH_2CH(R^{IV})\}_r O)R''SiO_{2/2}]_k [SiR''_2 O_{2/2}]_l [SiHR''O_{2/2}]_m \quad (15),$$

are prepared, where
$R^{IV}$ are hydrogen atoms or methyl radicals,
$R^V$ are methyl, ethyl, vinyl, allyl or phenyl radicals,
h is 1 or 2,
z is from 1 to 20,
y is 1, 2, 3 or 4,
a is from 0 to 2,
r is from 0 to 20,
k is from 1 to 20,
l is from 0 to 200,
m is from 0 to 100 and
a+k+l+m is at least 4.

16. The process as claimed in claim 2, wherein the catalyst support materials are selected from the group consisting of $SiO_2$, $Al_2O_3$, aluminas, activated carbons, zeolites and organic resins.

17. The process as claimed in claim 2, wherein a temperature is from −10° C. to +200° C.

18. The process as claimed in claim 2 which is carried out in a batch, semibatch or continuous mode of operation.

19. The process as claimed in claim 1, where not more than 0.01 liter of solvent is used per mole of OR group formed.

* * * * *